United States Patent [19]

Dulog et al.

[11] 3,953,530

[45] Apr. 27, 1976

[54] PROCESS FOR MAKING o- AND p-CHLOROPHENOLS

[75] Inventors: Lothar G. Dulog, Sint Martens Latem; Sylvain A. R. Dewaele, Evergem, both of Belgium

[73] Assignee: S. A. Texaco Belgium N.V., Brussels, Belgium

[22] Filed: Jan. 10, 1972

[21] Appl. No.: 216,768

[52] U.S. Cl. .................. 260/623 R; 260/621 G; 260/621 R
[51] Int. Cl.² ........................................ C07C 39/28
[58] Field of Search ........ 260/623 R, 621 R, 621 G, 260/623 R, 610 R

[56] References Cited
UNITED STATES PATENTS 3,461,170   8/1969   Schmerling ..................... 260/613
3,600,447   8/1971   Vesely .............................. 260/621

OTHER PUBLICATIONS

Smith et al., "Jour. Chem. Soc.," pp. 2897–2905, (1963).

*Primary Examiner*—James O. Thomas, Jr.
*Assistant Examiner*—W. B. Lone
*Attorney, Agent, or Firm*—T. H. Whaley; C. G. Ries; Henry W. Archer

[57] ABSTRACT

Disclosed is a process for making ortho- and para-chlorophenols by treating alpha-cumylchloride with an aqueous hydrogen peroxide solution. The two products can be separated by distillation.

4 Claims, No Drawings

PROCESS FOR MAKING O- AND P-CHLOROPHENOLS

This invention is concerned with a novel process for preparing ortho- and parachlorophenols from a single starting compound.

As is well known, ortho-chlorophenol finds utility in the preparation of catechol. Para-chlorophenol is used in dye and fungicide manufacture and in the preparation of hydroquinone. The first of these compounds generally is synthesized by diazotizing o-chloroaniline in $H_2SO_4$ solution and then heating with 65% $H_2SO_4$ at 140°C, and also by sulfonating phenol, chlorinating, then splitting off the sulfonic acid group. Para-chlorophenol usually is obtained by chlorinating phenol with sulfuryl chloride. Thus the preparation of the compounds of interest requires fairly drastic conditions as regards temperature and nature of the reagents employed.

In accord with the present invention, it has been discovered that both phenols can be prepared under relatively mild operating conditions from the same starting compound.

The reaction whereby the subject compounds are obtained proceeds as follows:

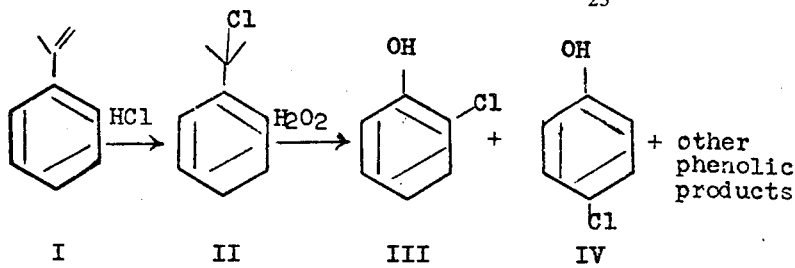

Alpha-cumychloride (II), which is obtained in nearly quantitative yield by the addition of hydrogen chloride gas to alpha-methyl-styrene (I) at −5 to 0°C, is reacted at about 40° to 100°C and preferably at 40° to 50°C, with 30% hydrogen peroxide. The latter must be added very slowly, over a period of 0.5 to 10 hours, because the reaction is very exothermic. After the addition, a reaction mass containing the phenolic fraction is obtained. The phenolic fraction is extracted from the reaction mass and the ortho- and pharachlorophenol (III and IV) are separated by distillation.

The invention is further illustrated but not limited by the following examples:

EXAMPLE 1

In a four-necked vessel provided with a mechanical stirrer, a thermometer dipping in the reaction liquid, a gas inlet and a reflux condenser is placed 100 parts by weight alpha-methyl-styrene (I). The stirrer is started, the vessel is cooled with an ice-salt bath to −5 to 0°C (internal temperature) and hydrogen chloride gas is bubbled through until the weight has increased to 132.5 parts by weight.

The gas inlet is replaced by a dropping funnel containing 171 parts by weight hydrogen peroxide (30%) solution. The temperature inside the vessel is kept at between 40° and 50°C and hydrogen peroxide is added over a period of 6 hours with rapid stirring. Then, the mixture is stirred for one more hour at 40° to 50°C and allowed to cool to room temperature. 150 parts by volume of NaOH (20%) are added and the aqueous layer is extracted 5 times with 25 parts by volume of benzene. The aqueous layer is acidified with concentrated hydrochloric acid (37%) and extracted 5 times with 25 parts by volume of benzene. The benzene or other non-polar solvent extracts are washed with water until neutral, dried over sodium sulfate and the solvent evaporated. The phenolic fraction obtained in this way is a dark brown oil and weighs 55.0 parts by weight (55 weight percent based on alpha-methyl-styrene (I) used). Distillation through a 60 cm Vigreux column gives:

1. Ortho-chlorophenol, bp 72°-79°C/15-27 mmHg, 7.8 parts by weight (7.15% yield), 97% pure.
2. Middle fraction, bp 74°-97°C/12-15 mmHg, 4.6 parts by weight of phenol (4.6% yield) 84.5% pure.
3. Para-chlorophenol, bp 97°-101°C/10-13 mmHg, 14.4 parts by weight (13.2% yield) 95% pure.
4. Para-cumylphenol, bp 197°-201°C/14 mmHg, 6.4 parts by weight (3.6% yield).

EXAMPLE 2

To 131 parts by weight alpha-cumylchloride are added dropwise 170 parts by weight hydrogen peroxide (30%) as in Example 1. During the addition the internal temperature is 47°C. 7.5 hours are required to complete the addition. The phenolic fraction is obtained as in Example 1, and amounts to 53.2 parts by weight (53.2 weight percent based on alpha-methyl styrene). Distillation through a column packed with Raschig rings gives:

1. Ortho-chlorophenol, bp 89°C/48 mmHg, 13.7 parts by weight (12.3% yield) 98% pure.
2. Para-chlorophenol, bp 100°-108°C/20 mmHg, 19.0 parts by weight (17.9% yield).
3. Para-cumylphenol, bp 177°-180°C/10 mmHg, 2.2 parts by weight (1.2% yield).

While in the foregoing specification certain presently preferred embodiments of the claimed invention have been disclosed, such disclosure has been by way of example only and it is not to be inferred therefrom that the invention is to be deemed specifically limited to the precise details thus disclosed.

Furthermore while the invention has been illustrated with particular reference to specific compounds in which the benzenoid moiety is unsubstituted, it will be understood by those skilled in the art of organic chemistry that there may be prepared by the process of this invention analogous compounds having one or more (lower) alkyl, halo or other non-interfering substituents on the benzene ring. Such derivatives fall within the purview of the subjoined claims.

What is claimed is:

1. A process for making ortho- and para- chlorophenols which comprises reacting alpha-cumylchloride with aqueous hydrogen peroxide at a temperature ranging from about 40 to about 100°C. and distilling the resulting reaction mass to recover said ortho and para chlorophenols.

2. The process according to claim 1, wherein 30% hydrogen peroxide is used.

3. The process according to claim 1, wherein said alpha-cumylchloride is obtained by adding hydrogen chloride gas to alpha-methyl styrene at −5 to 0°C.

4. The process of claim 1, wherein said hydrogen peroxide is added to said alpha-cumylchloride over a peroid ranging from about 0.5 to about 10 hours, the resulting reaction mixture is allowed to cool to about room temperature, sodium hydroxide is added to form an aqueous layer, said layer is acidified, with hydrochloric acid, extracted with a non-polar solvent following which the solvent extracts are washed with water until neutral, dried and the solvent is evaporated leaving an oil containing the desired products.

\* \* \* \* \*